United States Patent
Kemp et al.

(10) Patent No.: US 12,357,770 B2
(45) Date of Patent: Jul. 15, 2025

(54) GRASPER FOR A NEEDLE SHEATH, CAP, AUTOINJECTOR AND METHOD OF PRODUCING A GRASPER

(71) Applicant: SANOFI AVENTIS DEUTSCHLAND GMBH, Frankfurt am Main (DE)

(72) Inventors: Thomas Mark Kemp, Ashwell Hertfordshire (GB); Louise Hodgson, Stevenage Herts (GB); George Sykes, Melbourn Herts (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1044 days.

(21) Appl. No.: 17/345,720

(22) Filed: Jun. 11, 2021

(65) Prior Publication Data
US 2021/0338940 A1    Nov. 4, 2021

Related U.S. Application Data

(63) Continuation of application No. 15/579,144, filed as application No. PCT/EP2016/062459 on Jun. 2, 2016, now Pat. No. 11,045,610.

(30) Foreign Application Priority Data

Jun. 3, 2015   (EP) .................................... 15170595

(51) Int. Cl.
A61M 5/32   (2006.01)
A61M 5/20   (2006.01)

(52) U.S. Cl.
CPC ........ *A61M 5/3204* (2013.01); *A61M 5/2033* (2013.01); *A61M 5/3202* (2013.01); *A61M 2205/581* (2013.01); *A61M 2207/00* (2013.01)

(58) Field of Classification Search
CPC ............... A61M 5/20; A61M 2205/58; A61M 2207/10; A61M 5/2033; A61M 2205/581;
(Continued)

(56) References Cited

U.S. PATENT DOCUMENTS

2007/0112310 A1   5/2007   Lavi et al.
2009/0182284 A1   7/2009   Morgan
(Continued)

FOREIGN PATENT DOCUMENTS

CN   103476443   12/2013
CN   103492000    1/2014
(Continued)

OTHER PUBLICATIONS

International Preliminary Report on Patentability in International Appln. No. PCT/EP2016/062459, Dec. 5, 2017, 6 pages.
(Continued)

*Primary Examiner* — Jason E Flick
(74) *Attorney, Agent, or Firm* — Fish & Richardson P.C.

(57) ABSTRACT

The disclosure refers to a grasper for a needle sheath removably arranged over a needle, wherein the grasper comprises
a grasping carrier formed of a sheet and multiply bent along a plurality of longitudinal fold edges to form a plurality of carrier portions, wherein more than one of the plurality of carrier portions comprises a respective barb projecting from the surface of the carrier portion.
The disclosure further refers to a cap and an autoinjector and a method of producing a grasper.

20 Claims, 4 Drawing Sheets

(58) Field of Classification Search
CPC ............ A61M 2207/00; A61M 5/3202; A61M 5/3204
See application file for complete search history.

(56) References Cited

U.S. PATENT DOCUMENTS

| | | | |
|---|---|---|---|
| 2010/0016795 | A1 | 1/2010 | McLoughlin |
| 2012/0022937 | A1 | 1/2012 | Bhatia et al. |
| 2012/0157965 | A1* | 6/2012 | Wotton ................ A61K 9/0087 604/506 |
| 2012/0238961 | A1* | 9/2012 | Julian .................... A61M 5/20 29/700 |
| 2013/0092361 | A1 | 4/2013 | Wrazel et al. |
| 2014/0257192 | A1 | 9/2014 | Morgan et al. |
| 2014/0284275 | A1 | 9/2014 | Boccato et al. |
| 2014/0343503 | A1 | 11/2014 | Holmqvist |
| 2016/0144132 | A1 | 5/2016 | Scanlon |

FOREIGN PATENT DOCUMENTS

| | | |
|---|---|---|
| CN | 103608055 | 2/2014 |
| CN | 104023769 | 9/2014 |
| CN | 104136056 | 11/2014 |
| CN | 104136060 | 11/2014 |
| EP | 2361648 | 8/2011 |
| EP | 2361648 A1 * | 8/2011 .......... A61M 5/2033 |
| EP | 2607323 | 6/2013 |
| EP | 2823836 | 1/2015 |
| EP | 2823838 | 1/2015 |
| GB | 2445090 | 6/2008 |
| JP | H09-285542 | 11/1997 |
| JP | 2009-538662 A | 11/2009 |
| JP | 2011-528247 | 11/2011 |
| JP | 2014-530083 | 11/2014 |
| RU | 2009102986 | 8/2010 |
| WO | WO 2007/138299 A1 | 12/2007 |
| WO | WO 2009/081103 | 7/2009 |
| WO | WO 2009/090499 | 7/2009 |
| WO | WO 2012/110572 | 8/2012 |
| WO | WO 2012/110576 | 8/2012 |
| WO | WO 2013/057032 | 4/2013 |
| WO | WO 2013/058697 | 4/2013 |
| WO | WO 2013/076247 | 5/2013 |
| WO | WO 2013/076248 | 5/2013 |
| WO | WO 2014/154498 | 10/2014 |
| WO | WO 2015/004052 A1 | 1/2015 |
| WO | WO 2016/132187 | 8/2016 |

OTHER PUBLICATIONS

International Search Report and Written Opinion in International Appln. No. PCT/EP2016/062459, dated Sep. 1, 2016, 9 pages.

* cited by examiner

GRASPER FOR A NEEDLE SHEATH, CAP, AUTOINJECTOR AND METHOD OF PRODUCING A GRASPER

CROSS REFERENCE TO RELATED APPLICATIONS

The present application is a continuation of U.S. patent application Ser. No. 15/579,144, filed on Dec. 1, 2017, which is the national stage entry of International Patent Application No. PCT/EP2016/062459, filed on Jun. 2, 2016, and claims priority to Application No. EP 15170595.1, filed on Jun. 3, 2015, the disclosures of which are expressly incorporated herein in entirety by reference thereto.

TECHNICAL FIELD

The disclosure generally relates to a grasper for a needle sheath removably arranged on a needle. Furthermore, the disclosure relates to a cap comprising such a grasper and an autoinjector comprising such a cap with a grasper.

BACKGROUND

Administering an injection is a process which presents a number of risks and challenges for users and healthcare professionals, both mental and physical. Injection devices typically fall into two categories—manual devices and auto-injectors.

In a conventional manual device, manual force is required to drive a medicament through a needle. This is typically done by a plunger which has to be continuously pressed during the injection.

Auto injector devices may be single-use or reusable devices and aim to make self-injection easier for patients. A conventional autoinjector may completely or partially replace activities involved in parenteral drug delivery from a manual device. Typically, such activities include removal of a protective needle sheath, insertion of the needle, providing the force for administering the injection and possibly removal and shielding of the used needle.

To protect the needle of the device from damage or to protect people from needle-prick injuries before using of the device, the needle is covered by a protective needle cap or the so-called protective or rigid needle sheath (shortly named RNS).

In order to prepare the autoinjector device for delivering a dose, the protective needle sheath has to be removed from the needle. This may be done by gripping or grasping the protective needle sheath and pulling it away from the needle.

There remains a need for an improved grasper for the protective needle sheath and a cap with such an improved grasper and an autoinjector comprising such a cap with an improved grasper so that the protective needle sheath can be securely removed from the autoinjector.

SUMMARY

The present disclosure provides a grasper for the protective needle sheath and a cap with such a grasper and an autoinjector comprising such a cap with a so that the protective needle sheath can be securely removed from the autoinjector.

Exemplary embodiments are provided in the dependent claims.

According to the present disclosure, a grasper for a needle sheath removably arranged over a needle is provided, wherein the grasper comprises a grasping carrier which is formed of a sheet and which is multiply bent along a plurality of longitudinal fold edges to form a plurality of carrier portions, wherein more than one of the plurality of carrier portions comprises a respective barb projecting from the surface of the carrier portion.

According to another aspect of the present disclosure, a grasper for a needle sheath removably arranged over a needle is provided, wherein the grasper is formed as an injection moulding part comprising a grasping carrier with a plurality of angled carrier portions, wherein more than one of the plurality of carrier portions comprises a respective barb projecting from the surface of the carrier portion.

The barb, being bent from a single piece of sheet, is simple to manufacture, leading to high manufacturing yields and low part cost. Furthermore, the grasper is easy to assemble into an autoinjector cap or a needle sheath remover. The barbs allow automatic gripping and removal of the protective needle sheath when an autoinjector cap is removed.

According to an exemplary embodiment, the grasping carrier is a single piece of sheet metal. In particular, the grasping carrier is formed from a sheet of steel or aluminium. Alternatively, the grasping carrier may be formed as rigid plastic or an injection moulding part. A single piece of sheet metal allows a variety of shapes and thin thickness. A single piece of rigid plastic or injection moulding parts are manufactured easier and more cost-efficiently.

Moreover, in an initial state the grasping carrier is flat. In a bent state, the grasping carrier has a pipe-form or cylinder-form with a polygonal cross section, e.g. a multi-facetted form. This concept increases the strength and stiffness of the grasping carrier and reduces stamping operation to manufacture. The shape of the grasping carrier may be varied and such that the grasper encircles the needle sheath to such an extent that a mechanical attachment, e.g. a locking connection between the grasper and the needle sheath is created.

In an exemplary embodiment, the grasping carrier is bent in such a manner that the outer carrier portions are partly overlapped. Hence, in the final bent state, the grasping carrier has a nearly circular cross section. During manufacture, nesting is prevented and bulk packaging is allowed. Furthermore, the overlapped carrier portions in the final bent state allow compensating manufacturing tolerances of graspers.

In a further exemplary embodiment, at least two of the plurality of carrier portions comprise a cut-out from which the barbs are bent in the same direction. In particular, the barbs are bent inwards to engage and grip the protective needle sheath.

In a possible embodiment, the barbs have a hook-form or prong-form. In particular, the barbs formed as hooks dig into the outer surface of the protective needle sheath and form a positive and/or non-positive connection during removing of the protective needle sheath.

In a further embodiment, the grasping carrier comprises one or more retaining slots or retaining lugs. Due to the low wall thickness of the grasping carrier, the grasping carrier can be assembled to an autoinjector cap of the autoinjector and both can be arranged to the protective needle sheath encasing the needle. The retaining slots or retaining lugs allow fixing of the grasping carrier and thus of the grasper in the autoinjector cap so that, in use, if the autoinjector cap is moved away from the autoinjector, it takes the grasper and with the grasper the protective needle sheath with it and removes them from the autoinjector and thus from the needle.

In a possible embodiment, the retaining lugs and the barbs are radially bent in opposite directions from the grasping carrier. In particular, the retaining lugs are bent outwards to grip, e.g. dig, into an inner cap surface of the autoinjector cap and the barbs are bent inwards to grip, e.g. dig, into the outer surface of the protective needle sheath. Furthermore, the retaining lugs and the barbs are bent in radial direction in different directions, namely outwards and inwards, and in axial direction in different directions, namely rearwards and forwards.

According to another aspect of the present disclosure, a cap for an autoinjector is provided wherein the cap comprises a grasper as described above. The cap is adapted to form a needle sheath remover and serves for a safe and easy assembling to the autoinjector wherein only axial force appears on the needle sheath during assembling so that needle damages are prevented and thus the needle will not be contaminated during assembly.

In an exemplary embodiment, a mounting support is arranged on an inner cap surface and adapted to retain the grasper in the cap. For example, the mounting support comprises holding lugs or holding slots corresponding to the retaining slots or retaining lugs of the grasper.

According to another aspect of the present disclosure, an autoinjector is provided wherein the autoinjector comprises a grasper as described above and a cap as described above, wherein the grasper is fixed in the cap and wherein the cap is removably arranged on the autoinjector.

In an exemplary embodiment, the cap and the grasper are connected in such a manner that removal of the cap together with the grasper from the autoinjector removes the needle sheath from the needle.

In a further exemplary embodiment, the barbs are adapted to deflect and grip the needle sheath during assembly of the needle sheath into the autoinjector and adapted to further grip the needle sheath when the cap is being removed from the autoinjector.

The barbs are bent radially inwards. The grasper is assembled into the cap in such a manner that the free ends of the angled barbs extend into the distal direction.

According to another aspect of the present disclosure, a method for producing a grasper is provided wherein the method comprises the steps:
    providing a grasping carrier in form of a sheet;
    forming a plurality of barbs into the grasping carrier by cutting, stamping or die cutting;
    multiply bending the grasping carrier along a plurality of longitudinal fold edges to form a plurality of carrier portions in such a manner that more than one of the plurality of carrier portions comprises a respective barb;
    bending the barbs in such a manner that the barbs project from an inner surface of the carrier portion.

Alternatively, the grasper as a single injection moulding part may be manufactured using injection moulding.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
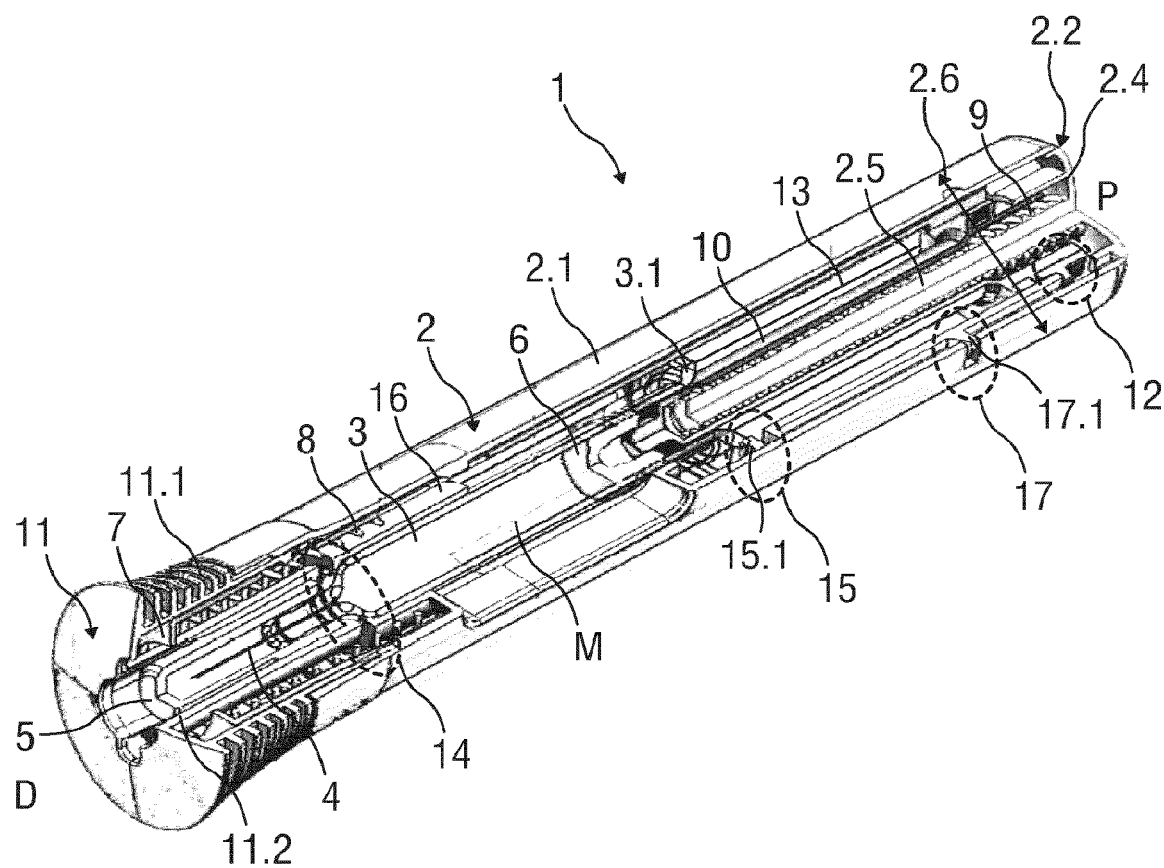
FIG. 1 is a schematic perspective partial section of an exemplary embodiment of an autoinjector.

FIG. 1 is a schematic perspective partial section of an exemplary embodiment of an autoinjector 1 in a state after assembly.

The autoinjector 1 comprises a housing 2 including a sleeve shaped front part 2.1 and a rear part 2.2. Alternatively, the housing 2 may be formed as a one-piece housing (not shown).

The housing 2 is adapted to hold a syringe 3, e.g. a glass syringe. The syringe 3 may be a pre-filled syringe containing a liquid medicament M and have a needle 4 arranged on a distal end. In another exemplary embodiment, the syringe 3 may be a cartridge which includes the medicament M and engages a removable needle (e.g., by threads, snaps, friction, etc.). In the shown exemplary embodiment, the syringe 3 is held in the housing 2 and supported at its proximal end 2.4 therein by a syringe support 15.

The autoinjector 1 further comprises a protective needle sheath 5 that is coupled to the needle 4. For example, the protective needle sheath 5 is removably coupled to the needle 4. The protective needle sheath 5 may be a rubber needle sheath or a rigid needle sheath (shortly named RNS) which is composed of rubber or a full or partial plastic shell.

A stopper 6 is arranged for sealing the syringe 3 in a proximal direction P and for displacing the medicament M contained in the syringe 3 through the needle 4.

The autoinjector 1 further comprises a sleeve-shaped needle shroud 7. In an exemplary embodiment, the needle shroud 7 is telescopically coupled to the housing 2 and movable between an extended position relative to the housing 2 in which the needle 4 is covered and a retracted position relative to the housing 2 in which the needle 4 is exposed. Furthermore, a shroud spring 8 is arranged to bias the needle shroud 7 in a distal direction D against the housing 2.

A drive spring 9 in the shape of a compression spring is arranged within a proximal part of the housing 2, in particular the rear part 2.2. A plunger 10 serves for forwarding the force of the drive spring 9 to the stopper 6. In an exemplary embodiment, the plunger 10 is hollow and the drive spring 9 is arranged within the plunger 10, biasing the plunger 10 in the distal direction D against the rear part 2.2. In another exemplary embodiment, the plunger 10 may be solid and the drive 9 may engage a proximal end 2.4 of the plunger 10. Likewise, the drive spring 9 could be wrapped around the outer diameter of the plunger 10 and extend within the syringe 3.

A plunger release mechanism 12 is arranged for preventing release of the plunger 10 prior to depression of the needle shroud 7 and for releasing the plunger 10 once the needle shroud 7 is sufficiently depressed.

In an exemplary embodiment, the autoinjector 1 further comprises at least one audible indicator 13 for producing an audible feedback for a user or patient indicating that medicament delivery is complete. In other words: The audible indicator 13 is adapted to indicate to a user or a patient that the full dose of medicament M was spent. The audible indicator 13 is formed for example as a bistable spring and is held in the rear part 2.2.

To allow an accurate support of the syringe 3 during and after assembly, the autoinjector 1 comprises a carrier 16 adapted to mount and hold the syringe 3 within the housing 2 in a forward or distal direction D.

Due to manufacturing tolerance, syringes 3 may have variable lengths. Thus, a flange 3.1 of the syringe 3 protrudes the carrier 16 in the proximal direction P. To support the axial position of the syringe 3 relative to the housing 2 after assembly, in particular during storage, transportation and normal use, the syringe support 15 comprises one or more supporting beams 15.1 extend radially inwards or longitudinally to accommodate the variable length of the syringe 3 in an assembled state. The supporting beams 15.1 are adapted to axially bias the syringe 3 in the distal direction D within the housing 2 and to compensate the variable length of the syringe 3 in the distal direction D.

Furthermore, the autoinjector 1 comprises a cap 11 that may be removably disposed at a distal end of the housing 2, in particular at a distal end of the front part 2.1. The cap 11 may comprise outer grip features 11.1 for facilitating removal of the cap 11, e.g., by twisting and/or pulling the cap 11 off the case 2.

The cap 11 may further include a grasper 11.2 arranged to engage and grip the protective needle sheath 5. The grasper 11.2 forms an inner grip element and is fixed to the cap 11.

The cap 11 is adapted to form a needle sheath remover. For this purpose, the cap 11 and the grasper 11.2 are connected in such a manner that removal of the cap 11 together with the fixed grasper 11.2 from the autoinjector 1 removes the protective needle sheath 5 from the needle 4. In other words: The grasper 11.2 is coupled to the cap 11 in a manner that when the cap 11 is removed, the protective needle sheath 5 is also removed from the needle 4.

Furthermore, a shroud pre-lock mechanism 14 is arranged to prevent depression of the needle shroud 7 when the cap 11 is in place, thus avoiding unintentional activation of the autoinjector 1, e.g. if dropped, during shipping or packaging, etc.

Figure 2A:
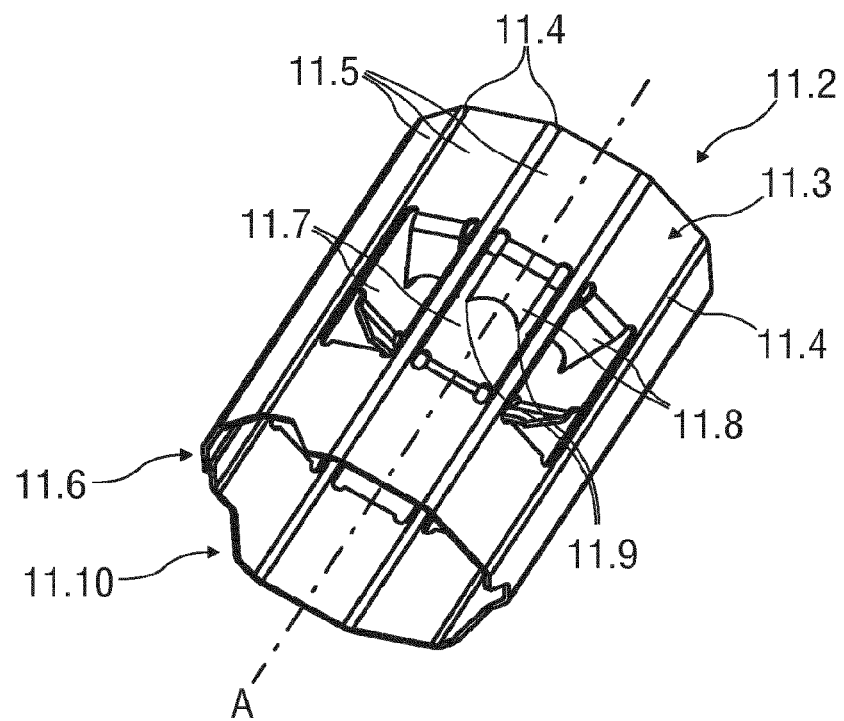
FIGS. 2A and 3 are perspective views of an exemplary embodiment of a grasper formed of single piece of a sheet.
Figure 2B:
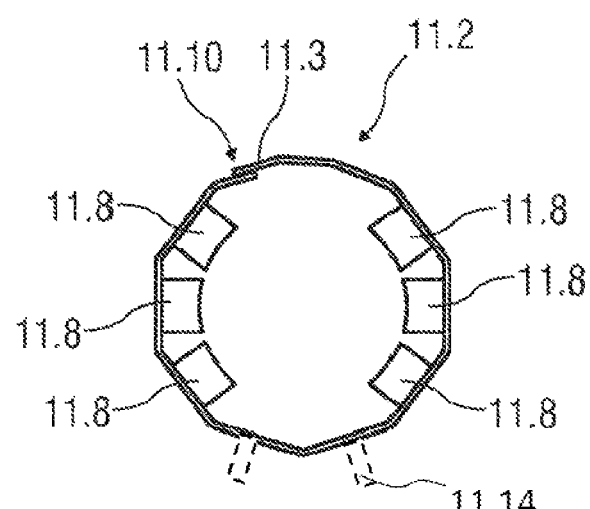
FIG. 2B is a cross section of an exemplary embodiment of a grasper.
Figure 3:
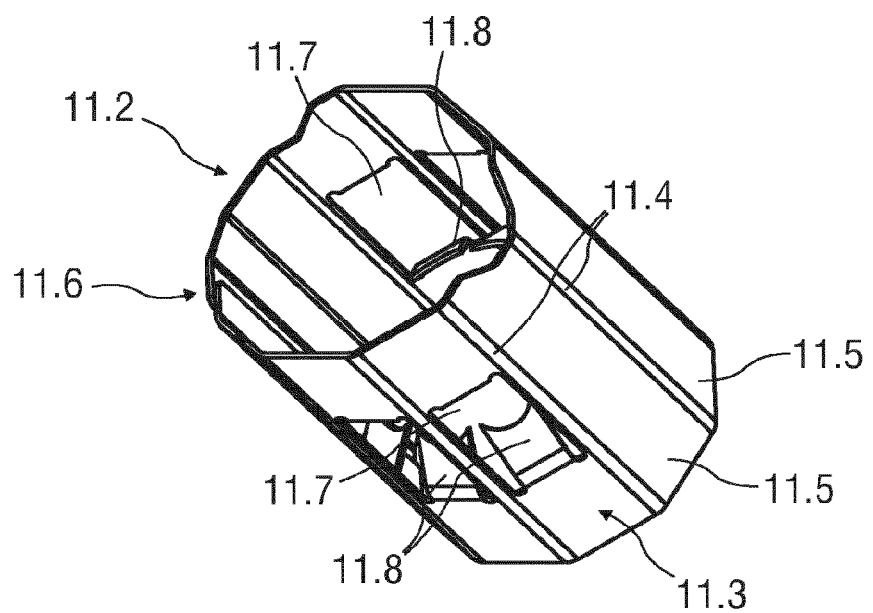

FIGS. 2A and 3 show an exemplary embodiment of a grasper 11.2 formed of single piece. FIG. 2B shows an exemplary embodiment of a cross section of the grasper 11.2.

The grasper 11.2 comprises at least a grasping carrier 11.3. The grasping carrier 11.3 is multiply bent along a plurality of longitudinal fold edges 11.4 to form a plurality of carrier portions 11.5. Furthermore, the grasping carrier 11.3 is bent or angled in such a manner that the outer carrier portions 11.5 are partly overlapped in an overlapping area 11.6. Hence, in the bent state the grasping carrier 11.3 has a pipe-form with a polygonal cross section. The partly overlapped area 11.6 in the bent state of the grasping carrier 11.3 allows compensation of manufacturing tolerances of the grasper 11.2.

To grip the protective needle sheath 5, more than one of the plurality of carrier portions 11.5 comprises a cut-out 11.7 from which a respective barb 11.8 is bent and projected inwards from the inner surface of the grasping carrier 11.3 and thus of the carrier portions 11.5. In the assembled state, the inwardly angled barbs 11.8 extend in the distal direction D of the autoinjector 1.

The barbs 11.8 are adapted to deflect and grip the protective needle sheath 5 during assembly of the needle sheath 5 into the autoinjector 1 and adapted to further grip the needle sheath 5 when the cap 11 is being removed from the autoinjector 1.

The barbs 11.8 are designed as hooks or have a prong-form. In particular, the barbs 11.8 are inwardly projected from the inner surface of the carrier portions 11.5 and comprise on its free end prongs 11.9. The prongs 11.9 are adapted to press onto or dig into the outer surface of the protective needle sheath 5 and to form an interference fit during assembling or a positive and/or non-positive connection at least during removing of the protective needle sheath 5. According to another aspect, the prongs 11.9 may be adapted to already dig into the outer surface of the protective needle sheath 5 when the grasper 11.2 is being assembled to the protective needle sheath 5 as described above.

According to the present embodiment, the prongs 11.9 are configured as double spikes respectively arranged on each barb 11.8. This configuration is realized by a concave shape respectively between two prongs 11.9 per barb 11.8. Due to the concave shape and thus controlling the distance between the prongs 11.9, a penetration depth into the surface of the protective needle sheath 5 may be limited. This is particularly important, when the protect needle sheath 5 is a rubber needle sheath where penetration could impact sterility by accessing the needle 4.

Furthermore, for correct orientation of the grasper 11.2 during assembling within the cap 11, the grasper 11.2 comprises an orientation element 11.10 indicating an assembling orientation. The orientation element 11.10 is designed as a tactile indicator or visual indicator or a combination of them. In particular, one of the front surfaces of the grasping carrier 11.3 is profiled, e.g. waved or pronged, and the other opposite front surface is even and flat.

Figure 4:
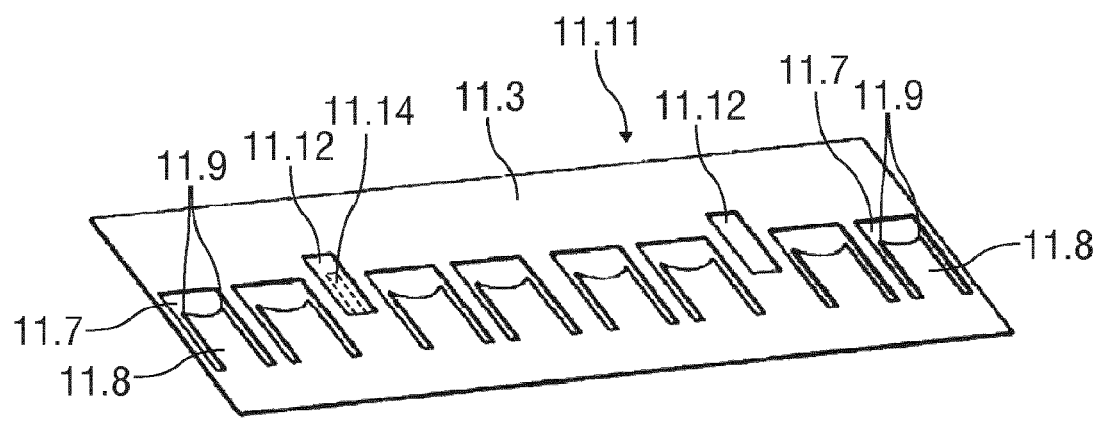
FIG. 4 is a perspective view of an exemplary embodiment of a single piece of a sheet.

FIG. 4 shows an exemplary embodiment of a single piece of a sheet 11.11 forming the grasper carrier 11.3.

According to an aspect of the present disclosure, the grasper 11.2 is produced by the following steps:
  providing the grasping carrier 11.3 in form of the sheet 11.11;
  forming a plurality of barbs 11.8 into the grasping carrier 11.3 by cutting, stamping or die stamping, where a distance between at least one group of barbs of the plurality of barbs 11.8 and another group of barbs of the plurality of barbs 11.8 is reduced when the sheet 11.11 is formed into the grasping carrier 11.3;
  multiply bending the grasping carrier 11.3 along a plurality of longitudinal fold edges 11.4 to form a plurality of carrier portions 11.5 in such a manner that more than one of the plurality of carrier portions 11.5 comprises a respective barb 11.8;
  bending the barbs 11.8 in such a manner that the barbs 11.8 project from an inner surface of the carrier portion 11.5 as it is shown in FIGS. 2 and 3.

The sheet 11.11 may be a single piece of sheet metal which is cut to form the cut-outs 11.7 and barbs 11.8 in the cut-outs 11.7.

Instead of the single-piece metal sheet, the grasper 11.2 may be formed as a single-piece plastic sheet or single-piece plastic part produced by injection moulding and bending or only by injection moulding. The alternative grasper 11.2 is formed as a single injection moulding part.

According to this alternative design of the grasper 11.2, the grasper 11.2 is manufactured by using injection moulding to form the grasping carrier 11.3 with angled carrier portions 11.5, wherein more than one of the plurality of carrier portions 11.5 comprises the respective inwardly angled barb 11.8 projecting from the surface of the carrier portion 11.5.

Regardless of the manufacturing method, the form and design of the grasper 11.2 made from a bent sheet or produced by injection moulding is the same. Hence, the described disclosure of the design and form of the grasper 11.2 applies to both embodiments.

To retain the grasper 11.2 within the cap 11, the sheet 11.11 comprises at least one retaining slot 11.12 formed by cutting into the grasping carrier 11.3. In the present embodiment, for example two retaining slots 11.12 are provided. The retaining slots 11.12 serve for retaining the grasper 11.2 within the cap 11 e.g. by holding lugs 11.13 of the cap 11 shown in FIG. 5.

In an alternative embodiment, for retaining the grasper 11.2 within the cap 11, the grasping carrier 11.3 may comprise retaining lugs 11.14 (dotted line) and the cap 11 may comprise holding slots (not shown). In this case, the optional retaining lugs 11.14 and the barbs 11.8 of the grasper 11.2 are radially bent in opposite directions from the grasping carrier 11.3.

In particular, the grasping carrier 11.3 is formed as an anchoring part comprising the plurality of barbs 11.8 or claws inwardly directed away from the grasping carrier 11.3 and at an angle in the direction to a longitudinal axis A of the grasper 11.2 and bearing against the outer surface of the needle sheath 5 to grip the needle sheath 5 wherein the retaining lugs 11.14 are outwardly bent and oriented at an angle away from the axis A and bearing against the inner cap surface of the cap 11 to grip the cap 11.

Figure 5:
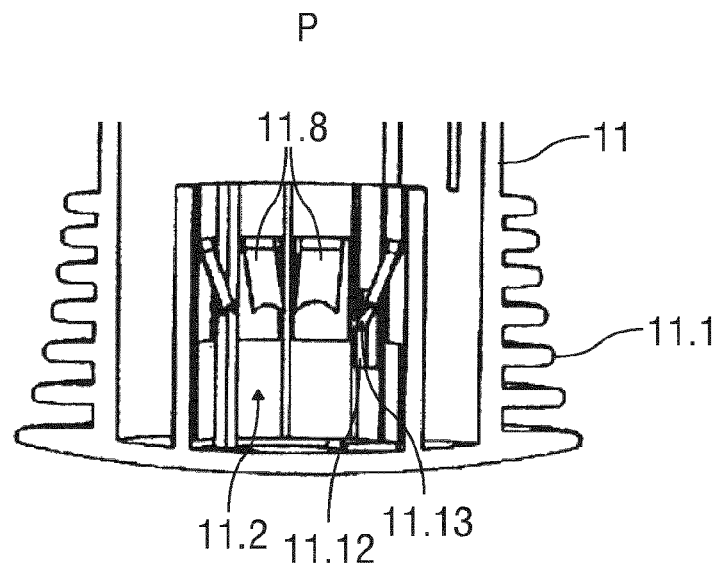
FIG. 5 is a cut-away view of an exemplary embodiment of a cap with an assembled grasper.

FIG. 5 is a cut-away view of an exemplary embodiment of a cap 11 with an assembled grasper 11.2 which is retained in the cap 11 by the holding lugs 11.13, engaging the retaining slots 11.12. The grasper 11.2 is fixed in the cap 11. The cap 11 comprises the outer grip feature 11.1 which may be gripped by a user to remove the cap 11 from the autoinjector 1 wherein the cap 11 takes the grasper 11.2 and with the grasper 11.2 the protective needle sheath 5 with it and removes them together from the autoinjector 1 and thus from the needle 4.

The barbs 11.8 are inwardly bent or angled and extend in the distal direction D to grasp the needle sheath 5 in the assembled state or at the latest during removing of the protective needle sheath 5 by removal of the cap 11.

Figure 6:
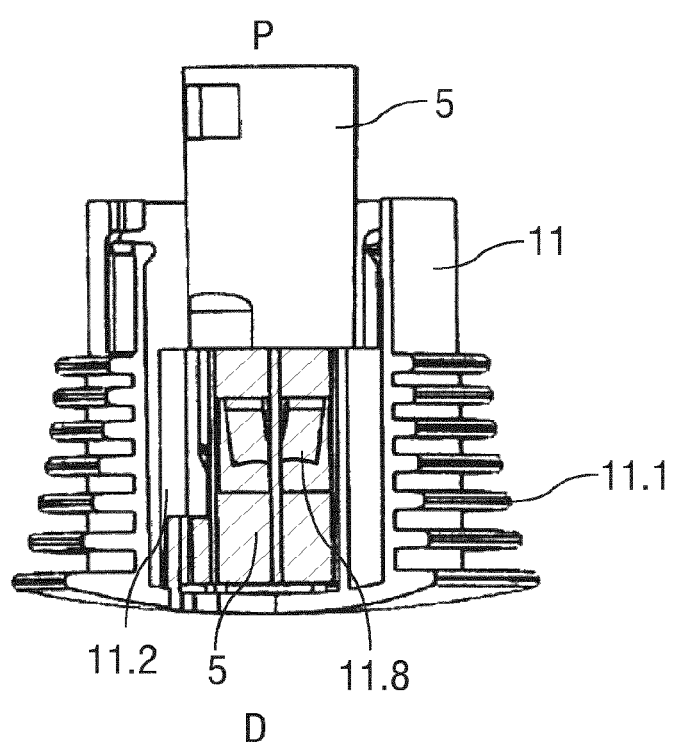
FIG. 6 is a cut-away view of an exemplary embodiment of a cap with an assembled grasper and an assembled protective needle sheath.

FIG. 6 is a cut-away view of an exemplary embodiment of a cap 11 with an assembled grasper 11.2 and a protective needle sheath 5 assembled in the grasper 11.2 by an interference fit of the barbs 11.8 and the needle sheath 5. The part of the needle sheath 5 which is retained in the grasper 11.2 is shown in a transparent manner to show the interference fit of the barbs 11.8 and the needle sheath 5.

Alternative to the interference fit of the barbs 11.8 and the needle sheath 5, the barbs 11.8 may be dug into the outer surface of the needle sheath 5 to form a mechanical locking connection, e.g. a force-locking connection, form-fitting connection and/or friction-locking connection by interlocking structures, hooks and eyes or protrusions and undercuts, profiled surfaces etc. at least during removing of the protective needle sheath 5.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, autoinjector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 autoinjector
2 housing
2.1 front part
2.2 rear part
2.4 proximal end
3 syringe
3.1 flange
4 needle
5 protective needle sheath
6 stopper
7 needle shroud
8 shroud spring
9 drive spring
10 plunger
11 cap
11.1 grip feature
11.2 grasper
11.3 grasping carrier
11.4 fold edges
11.5 carrier portion
11.6 overlapping area
11.7 cut-out
11.8 barb
11.9 prong
11.10 orientation element
11.11 sheet
11.12 retaining slot
11.13 holding lug
11.14 retaining lug
12 plunger release mechanism
13 audible indicator
14 shroud pre-lock mechanism
15 syringe support
15.1 supporting beam
16 carrier
D distal direction
M medicament
P proximal direction

The invention claimed is:

1. A grasper for a needle sheath configured to be removably arranged over a needle, wherein the grasper comprises a grasping carrier formed of a sheet of metal and comprising a plurality of groups of barbs projecting from a surface of the grasping carrier,
wherein each group of the plurality of groups of barbs comprises a respective plurality of barbs, and wherein the grasping carrier is such that when the sheet of metal is formed into the grasping carrier, a distance between at least one group of barbs and another group of barbs is reduced.

2. The grasper of claim 1, wherein the plurality of groups of barbs comprises three or more barbs, wherein a distance between adjacent barbs of the three or more barbs varies along a direction of the sheet of metal.

3. The grasper of claim 1, wherein the sheet of metal has a plurality of openings spaced apart from one another, the sheet of metal defining an entire perimeter of each of the plurality of openings.

4. The grasper of claim 3, wherein the plurality of groups of barbs comprise a barb deflectable into one of the plurality of openings.

5. The grasper of claim 1, wherein the plurality of groups of barbs project from the surface of the grasping carrier, wherein each barb of the plurality of groups of barbs is deflectable relative to the surface of the grasping carrier.

6. The grasper of claim 1, wherein a distance between adjacent barbs of one group of barbs is smaller than a distance between two adjacent groups of barbs.

7. A cap comprising:
a grasper for a needle sheath configured to be removably arranged over a needle, wherein the grasper comprises a grasping carrier formed of a sheet of metal and comprising a plurality of groups of barbs projecting from a surface of the grasping carrier;
wherein the grasper is retained in the cap, wherein the grasping carrier defines a distal opening of the grasper which faces a bottom of the cap,
wherein each group of the plurality of groups of barbs comprises a respective plurality of barbs, and wherein the grasping carrier is such that when the sheet of metal is formed into the grasping carrier, a distance between at least one group of barbs and another group of barbs is reduced.

8. The cap of claim 7, wherein the cap comprises a sleeve portion, which receives the grasper, wherein an outer surface of the sleeve portion faces an inner surface of a cap portion, the cap portion defining an exterior surface of the cap.

9. The cap of claim 8, wherein the cap portion comprises grip features on the exterior surface of the cap.

10. The cap of claim 7, wherein the cap comprises a sleeve portion, which receives the grasper, wherein at least one barb of the plurality of groups of barbs is arranged to engage a portion of the needle sheath, the portion of the needle sheath being closer to a distal end of the needle sheath than to a proximal end of the needle sheath.

11. The cap of claim 10, wherein the distal end of the needle sheath faces towards the bottom of the cap.

12. A drug delivery device comprising:
a cap, the cap comprising a grasper for a needle sheath configured to be removably arranged over a needle, wherein the grasper comprises a grasping carrier formed of a sheet of metal and comprising a plurality of groups of barbs projecting from a surface of the grasping carrier,
wherein the grasper is retained in the cap, wherein the grasping carrier defines a distal opening of the grasper which faces a bottom of the cap; and
the needle sheath being engaged by at least one barb of the plurality of groups of barbs to remove the needle sheath together with the cap,
wherein each group of the plurality of groups of barbs comprises a respective plurality of barbs, and wherein the grasping carrier is such that when the sheet of metal is formed into the grasping carrier, a distance between at least one group of barbs and another group of barbs is reduced.

13. The drug delivery device of claim 12, wherein the drug delivery device further comprises a housing, the housing being adapted to hold a medicament container, wherein the cap is disposed at a distal end of the housing.

14. The drug delivery device of claim 13, wherein the cap is removable from the housing by pulling.

15. The drug delivery device of claim 13, wherein the cap is removable from the housing by twisting.

16. The drug delivery device of claim 13, wherein the drug delivery device comprises the medicament container, wherein the medicament container is a syringe with a needle, the needle being covered by the needle sheath.

17. The drug delivery device of claim 16, wherein the drug delivery device further comprises a carrier adapted to hold and mount the syringe within the housing.

18. The drug delivery device of claim 17, wherein a proximal end of the syringe protrudes from the carrier.

19. The drug delivery device of claim 16, wherein the drug delivery device further comprises:
 a plunger,
 a drive unit arranged to drive the plunger distally relative to the medicament container, and
 a sleeve-shaped needle shroud, which is movable relative to the housing to release the plunger.

20. The drug delivery device of claim 12, wherein the drug delivery device is an autoinjector.

* * * * *